US006740743B2

United States Patent
Herrmann et al.

(10) Patent No.: US 6,740,743 B2
(45) Date of Patent: May 25, 2004

(54) SCORPIAN TOXINS

(75) Inventors: Rafael Herrmann, Wilmington, DE (US); James F. Wong, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/044,359

(22) Filed: Jan. 11, 2002

(65) Prior Publication Data

US 2002/0160454 A1 Oct. 31, 2002

Related U.S. Application Data

(63) Continuation of application No. 09/599,416, filed on Jun. 22, 2000.
(60) Provisional application No. 60/140,227, filed on Jun. 22, 1999.

(51) Int. Cl.[7] ............................. C07H 21/04; C12Q 1/68
(52) U.S. Cl. ..................... 536/23.1; 536/24.3; 530/350; 435/320.1; 435/325
(58) Field of Search ............................... 536/23.1, 24.3; 530/350; 435/320.1, 325; 800/295

(56) References Cited

U.S. PATENT DOCUMENTS 4,925,664 A 5/1990 Jackson et al.

FOREIGN PATENT DOCUMENTS

| EP | 0 374 753 | 12/1989 |
|---|---|---|
| WO | 94/28114 | 12/1994 |
| WO | 95/03065 | 2/1995 |

OTHER PUBLICATIONS

Selisko et al. "Cobatoxins 1 and 2 from *Centruroides noxius* Hoffmann constitute a subfamily of potassium–cahnnel–blocking scorpion toxins" Eur. J. Biochem. vol. 254, pp. 468–479, 1998.*
Genbank Accession No. Q9TVX3. Wu et al. "Neurotoxin BmP05 precursor". Jun. 15, 2002.*
Genbank Accession No. A59440. Xy et a. "Neurotoxin BmK37". Jun. 30, 2002.*
Genbank Accession No. AAB60781. Hermann et al. *Scorpion leiuropeptide I protein*. Dec. 28, 2000.*
Genbank Accession No. AAY99584. Hermann et al. "*Androctonus australis* potassium channel agonist kaliotoxin 2 precursor." Dec. 28, 2000.*
Genbank Accession No. AAB60782. Hermann et al. *Scorpion leiuropeptide III protein*. Dec. 28, 2000.*
J. M. Sabatier et al., Int. J. Peptide Protein Res., vol. 43:486–495, 1994, Leiurotoxin I, a Scorpion Toxin Specific for Ca2+–activated K+ Channels.
Eliahu Zlotkin, Phytoparasitica, vol. 19(3):177–183, 1991, Venom Neurotoxins—Models for Selective Insecticides.

Barbara Selisko et al., Eur. J. Biochem., vol. 254:468–479, 1998, Cobatoxins 1 and 2 from *Centruroides Noxius* Hoffmann constitute a Subfamily of Potassium–channel–blocking Scorpion Toxins.
Fatima Laraba–Djebari et al., Journ. of Biol. Chem., vol. 269(52):32835–32843, 1994, The Kaliotoxin Family Enlarged.
Eric Buisine et al., J. Peptide Res., vol. 49:545–555, 1997, Characterization of a New Family of Toxin–Like Peptides from the Venom of the Scorpion *Leiurus Quinquestriatus Hebraeus*.
Jose C. Martins et al., FEBS Letters, vol. 260(2):249–253, 1990, Solution Conformation of Leiurotoxin I (scyllatoxin) by 1H Nuclear Magnetic Resonance.
J.P. Ross et al., Toxicon, vol. 23(1):113–125, 1985, Characterization of Ten Porteins from the Venom of the Moroccan Scorpion *Androctonus Mauretanicus Mauretanicus*, Six of Which are Toxic to the Mouse.
D. L. Marshall et al., Toxicon, vol. 32(11):1433–1443, 1994, Neuromuscular Effects of Some Potassium Channel Blocking Toxins from the Venom of the Scorpion *Leiurus Quinquestriatus Hebreus*.
E. Zlotkin et al., Archives of Biochem. and Biophys., vol. 240(2):877–887, 1985, An Excitatory and a Depressant Insect Toxin from Scorpion Venom both Affect Sodium Conductance and Possess a Common Binding Site.
E. Zlotkin et al., Biochimie, vol. 53:1073–1078, 1971, Purification and Properties of the Insect Toxin from the Venom of the Scorpion *Androctonus Australis Hector*.
National Center for Biotechnology Information General Identifier No. 2959750, Aug. 5, 1998.
National Center for Biotechnology Information General Identifier No. 1173377, Feb. 1, 1996.
National Center for Biotechnology Information General Identifier No. 1711347, May 30, 2000.
National Center for Biotechnology Information General Identifier No. 1711349, May 30, 2000.
National Center for Biotechnology Information General Identifier No. 134302, Oct. 1, 2000.
Gary G. Chiochi et al., Journ. of Biol. Chem., vol. 263(21):10192–10197, 1988, Purification and Characterization of a Unique, Potent Inhibitor of Apamin Binding from *Leiurus Quinquestriatus Hebraeus* Venom.

(List continued on next page.)

*Primary Examiner*—Gary Benzion
*Assistant Examiner*—Jeanine A Goldberg

(57) ABSTRACT

This invention relates to an isolated nucleic acid fragment encoding scorpion toxins that are K-channel modifiers. The invention also relates to the construction of a chimeric gene encoding all or a substantial portion of the K-channel modifier, in sense or antisense orientation, wherein expression of the chimeric gene results in production of altered levels of the K-channel modifier in a transformed host cell.

8 Claims, 8 Drawing Sheets

OTHER PUBLICATIONS

Patrick Auguste et al., Journ. of Biol. Chem., vol. 265(8):4753–4759, 1990, Leiurotoxin I (Scyllatoxin), a Peptide Ligand for Ca2+–activated K+ channels.

National Center for Biotechnology Information General Identifier No. 134379, Nov. 1, 1995.

National Center for Biotechnology Information General Identifier No. 1173380, Nov. 1, 1995.

National Center for Biotechnology Information General Identifier No. 4389290, Jun. 16, 1998.

Eric Blanc et al., Biochemistry, vol. 37:12412–12418, 1998, Solution Structure of Two New Toxins from the Venom of the Chinese Scorpion *Buthus Martensi* Karsch Blockers of Potassium Channels.

Maria L. Garcia et al., Biochemistry, vol. 33:6834–6839, 1994, Purification and Characterization of Three Inhibitors of Voltage–Dependent K+ Channels from *Leiurus quinquestriatus var. hebraeus* Venom.

* cited by examiner

Figure 1

```
              *  ***    *            *   ***     *        *    *  ***  **        *     *  *  *
SEQ ID NO:21  MEGIAKITLILLFLFVTMHTFA NWNTEAAV C VYRT C DKD C KRRGYRSGK C INNA C K YPYGK
SEQ ID NO:02  MSRIFTILIV-FALNIIISLS  NFKVEAAQ C YSSD C RVK C AAMGFNSGK C INSK C K Y--K
              1                      ↑                                                    60
              \_Signal Sequence_/    Start of Mature   _____Mature Peptide_____/
                                     peptide
```

Figure 2

```
                   *      **          *          *         *       *      *    *    *
SEQ ID NO:22   MKVFSAVLILFVCSMIIGINA-VRIPVS  C KHSGQ- C LKP  C KDA-GMRFGK C MNGK C D C TPK
SEQ ID NO:04   MKFFTSVLMMIIFSMVISSHAQYELDVT  C MGGADN C VKP  C YDKYGTTKTK C INDR C N C YP-
SEQ ID NO:06   MKFSSILLTLLICSMTICINCQVETNVK  C TGG--S C AST  C KRVIGVAAGK C INGR C V C YP-
               1                                                                      62
```

Figure 3

```
                   *  ** *  *  *  *  **** ** *   *  * * **
SEQ ID NO:23 ----------------------VG C EE C P MH C KGKNAKPT C DNGV C N C NV
SEQ ID NO:08 MSRLFTLVLIVLAMNVMMAIISDPGVEAVD C EE C P FH C AGKNAIPT C DDGE C N C NV
             1                                                                56
```

Figure 4

```
                  *  *** *  *  *  *  ****  *    *****    *  *   *  *** *
SEQ ID NO:24  ---------------------VS C ED C PDH C STQKARAK C DNDK C V C EPK
SEQ ID NO:10  MKMSRLYAIILIVLVMNVIMTIMPDSKVEAVG C ED C PEH C SQQNARAK C ENDK C V C EPK
              1                                                              59
```

Figure 5

```
                                                              *  *    **
                                                              *  **  *****   IG IG
                                                              *  **  *****   60
SEQ ID NO:25  ----------------------AF C NLRM C QLS C RSLGLLGK
SEQ ID NO:12  MIKELLSTEMYNYYKFVLIMVFFAATIIFSDINVEGAF C NLRR C QLI C RESGLLGK
              1

*   *   *
              *   *   *
              *   *   *
SEQ ID NO:25  DK  C E C VKH--
SEQ ID NO:12  DR  C E C VPHGK
              61                  70
```

Figure 6

```
                          *      *    ****  *    *   *  **  * ***   *   *    *
SEQ ID NO:26  ----------------- C GP  C FTTDPYTESK C AT CC GGR-GK C VGPQ C L NRI
SEQ ID NO:14  MKFLYGILIALFLTVMIATHSEAR C PN C FTTNPNAEAD C KK CC GNRWGK C AGYQ C V PMK
              1                                                                 60
```

Figure 7

```
                  ****                       *        *      *        ****     *    **    ****    *
SEQ ID NO:27  ------------------GLIDVR     C YDSRQ  C WIA  C KKVTGSTQGK  C QNKQ  C  C  Y
SEQ ID NO:16  MKILSVLLIALIICSLGVCIEAGLIDVR  C SASRE  C WEA  C RKVTGSGQGK  C QNNQ  C  C  Y
SEQ ID NO:18  MKILSVLLIALIICSISIYSEADLIDVK  C ISSQE  C WIA  C KKVTGRFQGK  C QNKQ  C  R  Y
              1                                                                         58
```

Figure 8

```
SEQ ID NO:28  ---------------XFTDVK C TGSKQ C WPV  C KQMFGKPNGK C MNGK C R C YS
SEQ ID NO:20  ILSVFLITFVICSIMISTEAQFIDVK C TSXKE C WPI C KERFGVARGK C INKQ C R C YS
              1                                                                57
```

SCORPIAN TOXINS

This application is a continuation application of U.S. Application No. 09/599,416, filed Jun. 22, 2000, which claims the benefit of U.S. Provisional Application No. 60/140,227, filed Jun. 22, 1999, whose contents are hereby incorporated by reference.

FIELD OF THE INVENTION

This invention is in the field of molecular biology. More specifically, this invention pertains to nucleic acid fragments encoding scorpion toxins that are potassium channel modifiers.

BACKGROUND OF THE INVENTION

Scorpion venoms have been recognized as a source of peptidyl inhibitors of various types of potassium ion (K) channels. Some of these peptides have been purified to homogeneity and their properties characterized. The most extensively studied of these toxins is charybdotoxin (ChTX). ChTX is a thirty-seven amino acid peptide isolated from venom of the old world scorpion *Leiurus quinquetriatus* var. *hebraeus*. Originally described as an inhibitor of the high-conductance, $Ca^{+2}$-activated K (Maxi-K) channel present in muscle and neuro-endocrine cells, ChTX was later found to also inhibit a number of different medium- and small-conductance $Ca^{+2}$-activated K-channels, as well as a voltage-dependent K-channel (K(v) 1.3). In each case, channel inhibition occurs with similar potency, in the low nanomolar range. A related toxin, iberiotoxin (IbTX), shares 68% sequence homology with ChTX and selectively blocks the Maxi-K channel. Other peptidyl inhibitors, such as limbatustoxin (LbTX) and kaliotoxin (KTX), have also been shown to possess greater selectivity for the Maxi-K channel. Other peptidyl toxins homologous to ChTX have been identified (e.g., noxiustoxin).

Potassium channels modulate a number of cellular events such as muscle contraction, neuro-endocrine secretion, frequency and duration of action potentials, electrolyte homeostasis, and resting membrane potential. These channels comprise a family of proteins that have been classified according to their biophysical and pharmacological characteristics. Inhibition of K-channels, in their role as modulators of the plasma membrane potential in human T-lymphocytes, has been postulated to play a role in eliciting immunosuppressive responses. In regulating membrane potential, K-channels play a role in the regulation of intracellular $Ca^{+2}$ homeostasis, which has been found to be important in T-cell activation.

Potassium channel modifiers are small polypeptides (31 to 37 amino acids) which form compact structures kept rigid by three disulfide bridges. Use of synthetic analogs with point mutations has determined that single amino acids residues are important for receptor binding and for biological activity of K-channel toxins (Sabatier et al. (1994) *Int. J. Peptide Protein Res.* 43:486–495). Moreover, a drug with high affinity for the receptor could be expected to produce irreversible blockade of synaptic transmission. When labeled with a tracer molecule, such a drug would provide a reliable way of tagging receptors to permit measurement of their number and distribution within cells and tissues. These features would have very valuable consequences for research on excitatory amino acid neurotransmission and for the development of therapeutic agents to treat central nervous system dysfunction in humans and animals. Methods for treating heart and neurological diseases by applying toxins derived from spiders have been described (U.S. Pat. No. 4,925,664).

Arthropod animals, including insects, and certain parasitic worms, use excitatory amino acids as a major chemical neurotransmitter at their neuromuscular junction and in their central nervous system. Because of the damage done by insect pests and the prevalence of parasitic worm infections in animals and humans in many countries, there is a constant need for potent and specific new pesticides and anthelmintic drugs that are non-toxic to humans, pets, and farm animals.

Many arthropods produce a mixture of insecticidal proteins referred to as venom. These toxic substances are synthesized in specialized glandular tissues, which, when directed by a stinging or piercing apparatus, are capable of paralyzing the arthropod's prey. Small, slow moving or stationary arthropods have adapted a strategy to instantaneously paralyze their prey by utilizing neurotoxic components of the venom at very low concentrations. These components, or neurotoxins, interfere with the function of insect nervous tissues through efficient competition for certain receptor sites. Many of these neurotoxins are polypeptides. These have been divided into different classes based on their host specificity and mode of action (Zlotkin (1991) *Phytoparasitica* 19:177–182). For example, neurotoxic peptides isolated from numerous species of scorpions have been divided into classes that affect arthropods and classes that affect mammals.

Due to a combination of problems associated with some synthetic insecticides, including toxicity, environmental hazards, and loss of efficacy due to resistance, there exists a continuing need for the development of novel means of invertebrate control, including the development of genetically engineered recombinant baculoviruses which express protein toxins capable of incapacitating the host more rapidly than the baculovirus infection per se.

Many different toxins have been isolated from scorpions. Cobatoxin 1 and 2 are potassium channel blocking toxins isolated from scorpions and which have 32 amino acids and contain 3 disulfide bridges (Selisko et al. (1998) *Eur. J. Biochem.* 254:468–479). Isolated from scorpion venom, the kaliotoxin 2 precursor contains a 22 amino acid signal sequence and a 37 amino acid mature peptide which specifically binds to receptor sites in rat synaptosomes (Laraba-Djebari et al. (1994) *J. Biol. Chem.* 269:32835–32843). Leiuropeptides I, II and III are peptides with cysteine pattern analogous to that of short-chain scorpion toxins. Leiuropeptide I acts on potassium channels, has 31 amino acids and a positively charged region that binds to receptors (Buisine E. et al. (1997) *J. Pept. Res.* 49:545–555). Leiurotoxin I is a 31 amino acid peptide with three disulfide bridges holding the amino-terminal alpha structure on the side of the carboxy-terminal two beta barrels (Martins et al. (1990) *FEBS Lett.* 260:249–253). The 35 amino acid neurotoxin P2 from the *Androctonus mauretanicus* scorpion is a structural homologue of the so called *Buthus epeus* insect toxins (Rosso and Rochat (1985) *Toxicon* 23:113–125). Having 36 residues and some overall homology to charybdotoxin and noxiustoxin, toxin 15–1 blocks calcium-activated potassium currents in muscle fibers (Marshall (1994) *Toxicon* 32:1433–1443).

Scorpion venoms have been identified as possible sources of compounds providing insecticidal properties. Two insect-selective toxins isolated from the venom of the scorpion *Leiurus quinquestriatus* and affecting sodium conductance have been reported previously (Zlotkin et al. (1985) *Arch. Biochem. Biophys.* 240:877–87). One toxin, AaIT, induced fast excitatory contractive paralysis of fly larvae and the other, LqhIT2, induced slow depressant flaccid paralysis suggesting that these two toxins have different chemical and pharmacological properties (Zlotkin et al. (1971) *Biochimie* (Paris), 53:1073–1078). Thus, other toxins derived from scorpion venom will also have different chemical and pharmacological properties.

SUMMARY OF THE INVENTION

The present invention concerns an isolated polynucleotide comprising a nucleotide sequence selected from the group consisting of: (a) a first nucleotide sequence of at least 81 nucleotides selected from the group consisting of SEQ ID NOs:1, 3, 5, 7, 9, 11, 13, 15, 17, and 19; (b) a second nucleotide sequence encoding a polypeptide of at least 27 amino acids having at least 80% identity based on the Clustal method of alignment when compared to a polypeptide selected from the group consisting of SEQ ID NOs:2, 4, 6, 8, 10, 12, 14, 16, 18, and 20; or (c) a third nucleotide sequence comprising the complement of the first or second nucleotide sequences.

In a second embodiment, this invention relates to an isolated polynucleotide encoding a mature K-channel agonist.

In a third embodiment, this invention concerns an isolated polynucleotide comprising a nucleotide sequence of at least one of 30 (preferably at least one of 40, most preferably at least 60) contiguous nucleotides derived from a nucleotide sequence selected from the group consisting of SEQ ID NOs:1, 3, 5, 7, 9, 11, 13, 15, 17, and 19 and the complement of such nucleotide sequences.

In a fourth embodiment, this invention relates to a chimeric gene comprising an isolated polynucleotide of the present invention operably linked to at least one suitable regulatory sequence.

In a fifth embodiment, the present invention concerns a host cell comprising a chimeric gene of the present invention or an isolated polynucleotide of the present invention. The host cell may be eukaryotic, such as a yeast or a plant cell, mammalian cell or an insect cell, or prokaryotic, such as a bacterial cell. The present invention also relates to a virus, preferably a baculovirus, comprising an isolated polynucleotide of the present invention or a chimeric gene of the present invention.

In a sixth embodiment, the invention also relates to a process for producing a host cell comprising a chimeric gene of the present invention or an isolated polynucleotide of the present invention, the process comprising either transforming or transfecting a compatible host cell with a chimeric gene or isolated polynucleotide of the present invention.

In a seventh embodiment, the invention concerns a K-channel agonist polypeptide of at least 27 amino acids comprising at least 80% identity based on the Clustal method of alignment compared to a polypeptide selected from the group consisting of SEQ ID NOs:2, 4, 6, 8, 10, 12, 14, 16, 18, and 20.

In an eighth embodiment, the invention concerns a method of obtaining a nucleic acid fragment encoding a substantial portion of a scorpion K-channel agonist polypeptide, comprising the steps of: synthesizing an oligonucleotide primer comprising a nucleotide sequence of at least one of 30 (preferably at least 40, most preferably at least one of 60) contiguous nucleotides derived from a nucleotide sequence selected from the group consisting of SEQ ID NOs:1, 3, 5, 7, 9, 11, 13, 15, 17, and 19, and the complement of such nucleotide sequences; and amplifying a nucleic acid fragment (preferably a cDNA inserted in a cloning vector) using the oligonucleotide primer. The amplified nucleic acid fragment preferably will encode a substantial portion of a scorpion K-channel agonist amino acid sequence.

In a tenth embodiment, this invention relates to a method of obtaining a nucleic acid fragment encoding all or a substantial portion of the amino acid sequence encoding a scorpion K-channel agonist polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing a cDNA or genomic fragment that comprises the isolated DNA clone.

In an eleventh embodiment, this invention concerns a composition, such as a hybridization mixture, comprising an isolated polynucleotide or an isolated polypeptide of the present invention.

In a twelfth embodiment, this invention concerns a method for expressing a gene encoding a scorpion K-channel agonist in the genome of a recombinant baculovirus in insect cell culture or in viable insects wherein said insect cells or insects have been genetically engineered to express a potassium channel blocking toxin 15-1, a Bmtx 1, a neurotoxin P2, a leiurotoxin I, a leiuropeptide I, a leiuropeptide III, a kaliotoxin 2 precursor or a cobatoxin 1. The recombinant baculovirus expression vector comprising a DNA sequence encoding a polypeptide of at least 27 amino acids comprising an amino acid sequence selected from the group consisting of SEQ ID NOs:2, 4, 6, 8, 10, 12, 14, 16, 18 and 20.

BRIEF DESCRIPTION OF THE DRAWINGS AND SEQUENCE LISTING

The invention can be more fully understood from the following detailed description, the accompanying drawings, and the Sequence Listing which form a part of this application.

FIG. 1 depicts the amino acid sequence alignment between the cobatoxin 1 from *Centruroides noxius* (NCBI General Identifier No. 2959750; SEQ ID NO:21) and the instant scorpion clone ibj1c.pk007.k8 (SEQ ID NO:2). The top row indicates with asterisks (*) the amino acids conserved in both sequences. The conserved cysteine residues probably involved in intrachain disulfide bridges are boxed.

FIG. 2 depicts the amino acid sequence alignment between the kaliotoxin 2 precursor from *Androctonus australis* (NCBI General Identifier No. 1173377; SEQ ID NO:22), the instant scorpion clone ibj1c.pk006.i20 (SEQ ID NO:4) and the instant scorpion clone ibj1c.pk009.i6 (SEQ ID NO:6). The top row indicates with asterisks (*) the amino acids conserved among all three sequences. The conserved cysteine residues probably involved in intrachain disulfide bridges are boxed.

FIG. 3 depicts the amino acid sequence alignment between the leiuropeptide I from *Leiurus quinquestriatus hebraeus* (NCBI General Identifier No. 1711347; SEQ ID NO:23) and the instant scorpion clone ibj1c.pk008.d3 (SEQ ID NO:8). The top row indicates with asterisks (*) the amino acids conserved in both sequences. The conserved cysteine residues probably involved in intrachain disulfide bridges are boxed.

FIG. 4 depicts the amino acid sequence alignment between the leiuropeptide III from *Leiurus quinquestriatus hebraeus* (NCBI General Identifier No. 1711349; SEQ ID NO:24) and the instant scorpion clone ibj1c.pk005.e21 (SEQ ID NO:10). The top row indicates with asterisks (*) the amino acids conserved in both sequences. The conserved cysteine residues probably involved in intrachain disulfide bridges are boxed.

FIG. 5 depicts the amino acid sequence alignment between the leiurotoxin I from *Leiurus quinquestriatus hebraeus* (NCBI General Identifier No. 134302; SEQ ID NO:25) and the instant scorpion clone ibj1c.pk007.c13 (SEQ ID NO:12). The top row indicates with asterisks (*) the amino acids conserved in both sequences. The conserved cysteine residues probably involved in intrachain disulfide bridges are boxed.

FIG. 6 depicts the amino acid sequence alignment between the neurotoxin P2 from *Androctonus mauretanicus* (NCBI General Identifier No. 134379; SEQ ID NO:26) and the instant scorpion clone ibj1c.pk0002.f9 (SEQ ID NO:14). The top row indicates with asterisks (*) the amino acids conserved in both sequences. The conserved cysteine residues probably involved in intrachain disulfide bridges are boxed.

FIG. 7 depicts the amino acid sequence alignment between the potassium channel blocking toxin 15-1 from *Leiurus quinquestriatus hebraeus* (NCBI General Identifier No. 1173380; SEQ ID NO:27), the instant scorpion clone ibj1c.pk006.h8 (SEQ ID NO:16) and the instant scorpion clone ibj1c.pk005.n9 (SEQ ID NO:18). The top row indicates with asterisks (*) the amino acids conserved in all three sequences. The conserved cysteine residues probably involved in intrachain disulfide bridges are boxed.

FIG. 8 depicts the amino acid sequence alignment between the Bmtx 1 from *Buthus Martensii* (NCBI Accession General Identifier No. 4389290; SEQ ID NO:28) and the instant scorpion clone ibj1c.pk007.g5 (SEQ ID NO:20). The top row indicates with asterisks (*) the amino acids conserved in both sequences. The conserved cysteine residues probably involved in intrachain disulfide bridges are boxed.

The following sequence descriptions and Sequence Listing attached hereto comply with the rules governing nucleotide and/or amino acid sequence disclosures in patent applications as set forth in 37 C.F.R. §1.821–1.825.

SEQ ID NO:1 is the nucleotide sequence comprising a substantial portion of the cDNA insert in clone ibj1c.pk007.k8 encoding an entire scorpion cobatoxin 1 with its entire signal sequence.

SEQ ID NO:2 is the deduced amino acid sequence of an entire scorpion cobatoxin 1 with its entire signal sequence derived from the nucleotide sequence of SEQ ID NO:1. The mature toxin without its signal sequence consists of amino acids 22 through 58.

SEQ ID NO:3 is the nucleotide sequence comprising a substantial portion of the cDNA insert in clone ibj1c.pk006.i20 encoding an entire scorpion kaliotoxin 2 precursor with its entire signal sequence.

SEQ ID NO:4 is the deduced amino acid sequence of an entire scorpion kaliotoxin 2 precursor with its entire signal sequence derived from the nucleotide sequence of SEQ ID NO:3. The mature toxin without its signal sequence consists of amino acids 23 through 61.

SEQ ID NO:5 is the nucleotide sequence comprising a substantial portion of the cDNA insert in clone ibj1c.pk009.i6 encoding an entire scorpion kaliotoxin 2 precursor with its entire signal sequence.

SEQ ID NO:6 is the deduced amino acid sequence of an entire scorpion kaliotoxin 2 precursor with its entire signal sequence derived from the nucleotide sequence of SEQ ID NO:5. The mature toxin without its signal sequence consists of amino acids 23 through 59.

SEQ ID NO:7 is the nucleotide sequence comprising a substantial portion of the cDNA insert in clone ibj1c.pk008.d3 encoding an entire scorpion leiuropeptide I with its entire signal sequence.

SEQ ID NO:8 is the deduced amino acid sequence of an entire scorpion leiuropeptide I with its entire signal sequence derived from the nucleotide sequence of SEQ ID NO:7. The mature toxin without its signal sequence consists of amino acids 29 through 56.

SEQ ID NO:9 is the nucleotide sequence comprising a substantial portion of the cDNA insert in clone ibj1c.pk005.e21 encoding an entire scorpion leiuropeptide III with its entire signal sequence.

SEQ ID NO:10 is the deduced amino acid sequence of an entire scorpion leiuropeptide III with its entire signal sequence derived from the nucleotide sequence of SEQ ID NO:9. The mature toxin without its signal sequence consists of amino acids 31 through 59.

SEQ ID NO:11 is the nucleotide sequence comprising a substantial portion of the cDNA insert in clone ibj1c.pk007.c13 encoding an entire scorpion leiurotoxin I with its entire signal sequence.

SEQ ID NO:12 is the deduced amino acid sequence of an entire scorpion leiurotoxin I with its entire signal sequence derived from the nucleotide sequence of SEQ ID NO:11. The mature toxin without its signal sequence consists of amino acids 38 through 70.

SEQ ID NO:13 is the nucleotide sequence comprising a substantial portion of the cDNA insert in clone ibj1c.pk0002.f9 encoding an entire scorpion neurotoxin P2 with its entire signal sequence.

SEQ ID NO:14 is the deduced amino acid sequence of an entire scorpion neurotoxin P2 with its entire signal sequence derived from the nucleotide sequence of SEQ ID NO:13. The mature toxin without its signal sequence consists of amino acids 24 through 60.

SEQ ID NO:15 is the nucleotide sequence comprising a substantial portion of the cDNA insert in clone ibj1c.pk006.h8 encoding an entire scorpion potassium channel blocking toxin 15-1 with its entire signal sequence.

SEQ ID NO:16 is the deduced amino acid sequence of an entire scorpion potassium channel blocking toxin 15-1 with its entire signal sequence derived from the nucleotide sequence of SEQ ID NO:15. The mature toxin without its signal sequence consists of amino acids 23 through 58.

SEQ ID NO:17 is the nucleotide sequence comprising a substantial portion of the cDNA insert in clone ibj1c.pk005.n9 encoding an entire scorpion potassium channel blocking toxin 15-1 with its entire signal sequence.

SEQ ID NO:18 is the deduced amino acid sequence of an entire scorpion potassium channel blocking toxin 15-1 with its entire signal sequence derived from the nucleotide sequence of SEQ ID NO:17. The mature toxin without its signal sequence consists of amino acids 23 through 58.

SEQ ID NO:19 is the nucleotide sequence comprising a substantial portion of the cDNA insert in clone ibj1c.pk007.g5 encoding an entire scorpion Bmtx1 with a portion of its signal sequence.

SEQ ID NO:20 is the deduced amino acid sequence of an entire scorpion Bmtx 1 with a portion of its signal sequence derived from the nucleotide sequence of SEQ ID NO:19. The mature toxin without its signal sequence consists of amino acids 21 through 57.

SEQ ID NO:21 is the amino acid sequence of the *Centruroides noxius* cobatoxin 1 having NCBI General Identifier No. 2959750.

SEQ ID NO:22 is the amino acid sequence of the *Androctonus australis* kaliotoxin 2 precursor having NCBI General Identifier No. 1173377.

SEQ ID NO:23 is the amino acid sequence of the *Leiurus quinquestriatus hebraeus* Leiuropeptide I having NCBI General Identifier No. 1711347.

SEQ ID NO:24 is the amino acid sequence of the *Leiurus quinquestriatus hebraeus* leiuropeptide III having NCBI General Identifier No. 1711349.

SEQ ID NO:25 is the amino acid sequence of the *Leiurus quinquestriatus hebraeus* leiurotoxin I having NCBI General Identifier No. 134302.

SEQ ID NO:26 is the amino acid sequence of the *Androctonus mauretanicus* neurotoxin P2 having NCBI General Identifier No. 134379.

SEQ ID NO:27 is the amino acid sequence of the *Leiurus quinquestriatus hebraeus* potassium channel blocking toxin 15-1 having the NCBI General Identifier No. 1173380.

SEQ ID NO:28 is the amino acid sequence of the *Buthus Martensii* Bmtx 1 having NCBI General Identifier No. 4389290.

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 30 preferably at least 40, most preferably at least 60 contiguous nucleotides derived from SEQ ID NOs:1, 3, 5, 7, 9, 11, 13, 15, 17, and 19, or the complement of such sequences.

"NPV" stands for nuclear polyhedrosis virus, a baculovirus. "Polyhedrosis" refers to any of several virus or viral diseases of insect larvae characterized by dissolution of tissues and accumulation of polyhedral granules in the resultant fluid. "PIBs" are polyhedral inclusion bodies. "AcNPV" stands for the wild-type *Autographa californica* nuclear polyhedrosis virus.

The term "isolated polynucleotide" refers to a polynucleotide that is substantially free from other nucleic acid sequences such as, and not limited to, other chromosomal and extrachromosomal DNA and RNA. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "substantially similar" refers to nucleic acid fragments wherein changes in one or more nucleotide bases results in substitution of one or more amino acids, but do not affect the functional properties of the polypeptide encoded by the nucleotide sequence. It is therefore understood that the invention encompasses more than the specific exemplary nucleotide or amino acid sequences and includes functional equivalents thereof. The terms "substantially similar" and "corresponding substantially" are used interchangeably herein.

For example, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Each of the proposed modifications is well within the routine skill in the art, as is determination of retention of biological activity of the encoded products.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6× SSC, 0.5% SDS at room temperature for 15 min, then repeated with 2× SSC, 0.5% SDS at 45° C. for 30 min, and then repeated twice with 0.2× SSC, 0.5% SDS at 50° C. for 30 min. A more preferred set of stringent conditions uses higher temperatures in which the washes are identical to those above except for the temperature of the final two 30 min washes in 0.2× SSC, 0.5% SDS which was increased to 60° C. Another preferred set of highly stringent conditions uses two final washes in 0.1× SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410; see also www.ncbi.nlm.nih.gov/BLAST/). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular arthropod proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refers to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in a variety of cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, DNA fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

"3' Non-coding sequences" refers to nucleotide sequences located downstream of a coding sequence and includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense RNA" refers to an RNA transcript that includes the mRNA and can be translated into a polypeptide by the cell. "Functional RNA" refers to sense RNA, antisense RNA, ribozyme RNA, or other RNA that may not be translated but yet has an effect on cellular processes.

The term "operably linked" refers to the association of two or more nucleic acid fragments so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or anti sense RNA derived from the nucleic acid fragment of the invention. "Expression" may also refer to translation of mRNA into a polypeptide. "Overexpression" refers to the production of a gene product in transgenic organisms that exceeds levels of production in normal or non-transformed organisms.

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refer to the production of gene product(s) in transgenic organisms in amounts or proportions that differ from that of normal or non-transformed organisms.

A "signal sequence" is an amino acid sequence that is covalently linked to an amino acid sequence representing a mature protein. The signal sequence directs the protein to the secretory system (Chrispeels (1991) *Ann. Rev. Plant Phys. Plant Mol. Biol.* 42:21–53).

"Mature protein" refers to a post-translationally processed polypeptide; i.e., one from which any pre- or propeptides, including signal sequences, present in the primary translation product have been removed. "Precursor protein" refers to the primary product of translation of mRNA; i.e., with pre- and propeptides still present. Pre- and propeptides may be but are not limited to intracellular localization signals.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

It is understood that "an insect cell" refers to one or more insect cells maintained in vitro as well as one or more cells found in an intact, living insect.

Standard recombinant DNA and molecular cloning techniques used herein are well known in the art and are described more fully in Sambrook et al. *Molecular Cloning. A Laboratory Manual*; Cold Spring Harbor Laboratory Press: Cold Spring Harbor, 1989 (hereinafter "Maniatis").

"PCR" or "polymerase chain reaction" is well known by those skilled in the art as a technique used for the amplification of specific DNA segments (U.S. Pat. Nos. 4,683,195 and 4,800,159).

Nucleic acid fragments encoding at least a substantial portion of several scorpion K-channel agonists have been isolated and identified by comparison of random arthropod cDNA sequences to public databases containing nucleotide and protein sequences using the BLAST algorithms well known to those skilled in the art. Table 1 lists the proteins that are described herein, and the designation of the cDNA clones that comprise the nucleic acid fragments encoding these proteins.

TABLE 1

Potassium Channel Modifiers From *Buthotus judaicus* Telsons 48-Hours Post Milking

| Enzyme | Clone |
|---|---|
| Cobatoxin 1 | ibj1c.pk007.k8 |
| Kaliotoxin 2 Precursor | ibj1c.pk006.i20 |
| Kaliotoxin 2 Precursor | ibj1c.pk009.i6 |
| Leiuropeptide I | ibj1c.pk008.d3 |
| Leiuropeptide III | ibj1c.pk005.e21 |
| Leiurotoxin I | ibj1c.pk007.c13 |
| Neurotoxin P2 | ibj1c.pk0002.f9 |
| Potassium Channel Blocking Toxin 15-1 | ibj1c.pk006.h8 |
| Potassium Channel Blocking Toxin 15-1 | ibj1c.pk005.n9 |
| Bmtx 1 | ibj1c.pk007.g5 |

The nucleic acid fragments of the instant invention may be used to isolate cDNAs and genes encoding homologous proteins from the same or other arthropod species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain I reaction).

For example, genes encoding other potassium channel blocking toxin 15-1s, Bmtx toxins, neurotoxin P2s, leiurotoxin Is, leiuropeptide Is, leiuropeptide IIls, kaliotoxin 1 precursors or cobatoxin Is, either as cDNAs or genomic DNAs, could be isolated directly by using all or a substantial portion of the instant nucleic acid fragments as DNA hybridization probes to screen libraries from any desired arthropod employing methodology well known to those skilled in the art. Specific oligonucleotide probes based upon the instant nucleic acid sequences can be designed and synthesized by methods known in the art (Maniatis). Moreover, the entire sequence(s) can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding arthropod genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 30 (preferably at least 40, most preferably at least 60) contiguous nucleotides derived from a nucleotide sequence selected from the group consisting of SEQ ID NOs:1, 3, 5, 7, 9, 11, 13, 15, 17, and 19 and the complement of such nucleotide sequences may be used in such methods to obtain a nucleic acid fragment encoding a substantial portion of an amino acid sequence of a polypeptide.

The present invention relates to a method of obtaining a nucleic acid fragment encoding a substantial portion of a scorpion K-channel agonist polypeptide, preferably a substantial portion of an arthropod potassium channel blocking toxin 15-1, Bmtx toxin, neurotoxin P2, leiurotoxin I, leiuropeptide I, leiuropeptide III, kaliotoxin 1 precursor or cobatoxin 1 polypeptide, comprising the steps of: synthesizing an oligonucleotide primer comprising a nucleotide sequence of at least 30 (preferably at least 40, most preferably at least 60) contiguous nucleotides derived from a nucleotide sequence selected from the group consisting of SEQ ID NOs:1, 3, 5, 7, 9, 11, 13, 15, 17, and 19, and the complement of such nucleotide sequences; and amplifying a nucleic acid fragment (preferably a cDNA inserted in a cloning vector) using the oligonucleotide primer. The amplified nucleic acid fragment preferably will encode a substantial portion of a potassium channel blocking toxin 15-1, a Bmtx toxin, a neurotoxin P2, a leiurotoxin I, a leiuropeptide I, a leiuropeptide III, a kaliotoxin 1 precursor or a cobatoxin 1.

Availability of the instant nucleotide and deduced amino acid sequences facilitates inununological screening of cDNA expression libraries. Synthetic peptides representing substantial portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

In another embodiment, this invention concerns viruses and host cells comprising either the chimeric genes of the invention as described herein or an isolated polynucleotide of the invention as described herein. Examples of host cells which can be used to practice the invention include, but are not limited to yeast, bacteria, plants, mammals and insect.

The nucleic acid fragments of the instant invention may be used to create transgenic plants in which the disclosed K-channel modifiers are expressed. This would be useful as a means for controlling insect pests by producing plants that are more insect-tolerant than the naturally occurring variety.

Expression in plants of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) EMBO J. 4:2411–2418; De Almeida et al. (1989) Mol. Gen. Genetics 218:78–86), and thus that multiple events must be screened in order to obtain lines displaying the desired expression level and pattern. Such screening may be accomplished by Southern analysis of DNA, Northern analysis of mRNA expression, Western analysis of protein expression, LC-MS, or phenotypic analysis.

The instant polypeptides (or substantial portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded scorpion K-channel agonist. An example of a vector for high level expression of the instant polypeptides in a bacterial host is provided (Example 6).

Insecticidal baculoviruses have great potential to provide an environmentally benign method for agricultural insect pest control. However, improvements to efficacy are required in order to make these agents competitive with current chemical pest control agents. One approach for making such improvements is through genetic alteration of the virus. For instance, it may be possible to modify the viral genome in order to improve the host range of the virus, to increase the environmental stability and persistence of the virus, or to improve the infectivity and transmission of the virus. In addition, improving the rate at which the virus acts to compromise the infected insect would significantly enhance the attractiveness of insecticidal baculoviruses as adjuncts or replacements for chemical pest control agents. One method for increasing the speed with which the virus affects its insect host is to introduce into the baculovirus foreign genes that encode proteins that are toxic to the insect wherein death or incapacitation of the insect is no longer dependent solely on the course of the viral infection, but instead is aided by the accumulation of toxic levels of the foreign protein. The results are insecticidal recombinant baculoviruses.

Recombinant baculoviruses expressing the instant scorpion K-channel agonists (or substantial portions thereof) may be prepared by protocols now known to the art (e.g., Tomalski et al., U.S. Pat. No. 5,266,317, exemplifying neurotoxins from the insect-parasitic mites; McCutchen et al. (1991) Bio/Technology 9:848–852; Maeda et al. (1991) Virology 184:777–780, illustrating construction of a recombinant baculovirus expressing AaIT; also see O'Reilly et al. (1992) Baculovirus Expression Vectors: A Laboratory Manual, W. H. Freeman and Company, New York; King and Possee (1992) The Baculovirus Expression System, Chapman and Hall, London; U.S. Pat. No. 4,745,051). These methods of gene expression provide economical preparation of foreign proteins in a eukaryotic expression vector system, in many instances yielding proteins that have achieved their proper tertiary conformation and formed the proper disulfide bridges necessary for activity.

Commonly, the introduction of heterologous genes into the baculovirus genome occurs by homologous recombination between viral genomic DNA and a suitable "transfer vector" containing the heterologous gene of interest. These transfer vectors are generally plasmid DNAs that are capable of autonomous replication in bacterial hosts, affording facile genetic manipulation. Baculovirus transfer vectors also contain a genetic construct comprising a region of the viral genome that has been modified to include the following features (listed in the 5' to 3' direction): 1) viral DNA comprising the 5' region of a non-essential genomic region; 2) a viral promoter; 3) one or more DNA sequences encoding restriction enzyme sites facilitating insertion of heterologous DNA sequences; 4) a transcriptional termination sequence; and 5) viral DNA comprising the 3' region of a non-essential genomic region. A heterologous gene of interest is inserted into the transfer vector at the restriction site downstream of the viral promoter. The resulting construct comprises a chimeric gene wherein the heterologous gene is under the transcriptional control of the viral promoter and transcription termination sequences present on the transfer vector. Moreover, this chimeric gene is flanked by viral DNA sequences that facilitate homologous recombination at a non-essential region of the viral genome. Recombinant viruses are created by co-transfecting insect cells that are capable of supporting viral replication with viral genomic DNA and the recombinant transfer vector. Homologous recombination between the flanking viral DNA sequences present on the transfer vector and the homologous sequences on the viral genomic DNA takes place and results in insertion of the chimeric gene into a region of the viral genome that does not disrupt an essential viral function. The infectious recombinant virion consists of the recombined genomic DNA, referred to as the baculovirus expression vector, surrounded by a protein coat.

In a preferred embodiment, the non-essential region of the viral genome that is present on the transfer vector comprises the region of the viral DNA responsible for polyhedrin production. Most preferred is a transfer vector that contains the entire polyhedrin gene between the flanking sequences that are involved in homologous recombination. Recombination with genomic DNA from viruses that are defective in polyhedrin production (due to a defect in the genomic copy of the polyhedrin gene) will result in restoration of the polyhedrin-positive phenotype. This strategy facilitates identification and selection of recombinant viruses.

In another embodiment, baculoviral genomic DNA can be directly modified by introduction of a unique restriction enzyme recognition sequence into a non-essential region of the viral genome. A chimeric gene comprising the heterologous gene to be expressed by the recombinant virus and operably linked to regulatory sequences capable of directing gene expression in baculovirus-infected insect cells, can be constructed and inserted directly into the viral genome at the unique restriction site. This strategy eliminates both the need for construction of transfer vectors and reliance on homologous recombination for generation of recombinant viruses. This technology is described by Ernst et al. (Ernst et al. (1994) *Nuc. Acid Res.* 22: 2855–2856), and in WO94/28114.

Recombinant baculovirus expression vectors suitable for delivering genetically encoded insect-specific neurotoxins require optimal toxin gene expression for maximum efficacy. A number of strategies can be used by the skilled artisan to design and prepare recombinant baculoviruses wherein toxin gene expression results in sufficient quantities of toxin produced at appropriate times during infection in a functional form and available for binding to target cells within the insect host.

The isolated toxin gene fragment may be digested with appropriate enzymes and may be inserted into the pTZ-18R plasmid (Pharmacia, Piscataway, N.J.) at the multiple cloning site using standard molecular cloning techniques. Following transformation of *E. coli* DH5αMCR, isolated colonies may be chosen and the plasmid DNA prepared. Positive clones will be identified and sequenced with the commercially available forward and reverse primers.

*Spodoptera frugiperda* cells (Sf-9) may be propagated in ExCell® 401 media (JRH Biosciences, Lenexa, KS) supplemented with 3.0% fetal bovine serum. Lipofectin® (50 μL at 0.1 mg/mL, Gibco/BRL) may be added to a 50 μL aliquot of the transfer vector containing the toxin gene of interest (500 ng) and linearized polyhedrin-negative AcNPV (2.5 μg, Baculogold® viral DNA, Pharmigen, San Diego, Calif.). Sf-9 cells (approximate 50% monolayer) may be co-transfected with the viral DNA/transfer vector solution. The supernatant fluid from the co-transfection experiment may be collected at 5 days post-transfection and recombinant viruses may be isolated employing standard plaque purification protocols, wherein only polyhedrin-positive plaques will be selected (Granados, R. R., Lawler, K. A., *Virology* (1981), 108, 297–308).

To propagate the recombinant virus of interest, isolated plaques may be picked and suspended in 500 μL of ExCell® media supplemented with 2.5% fetal bovine serum. Sf-9 cells in 35 mM petri dishes (50% monolayer) may be inoculated with 100 μL of the viral suspension, and supernatant fluids collected at 5 days post infection. These supernatant fluids will be used to inoculate cultures for large scale propagation of recombinant viruses.

Expression of the encoded toxin gene by the recombinant baculovirus will be confirmed using a bioassay, LCMS, or antibodies. The presence of toxin activity in the recombinant viruses will be monitored in vivo. These assays involve comparison of biological activity of recombinant viruses to wild-type viruses. Third instar larvae of *H. virescens* are infected orally by consumption of diet that contains test and control viruses and the larvae monitored for behavioral changes and mortality.

Isolated plugs of a standard insect diet are inoculated with approximately 5000 PIBs of each virus. Individual larvae that have not fed for 12 h prior to beginning of the bioassay are allowed to consume the diet for 24 h. The larvae are transferred to individual wells in a diet tray and monitored for symptoms and mortality on a daily basis (Zlotkin et al. (1991) *Biochimie* (Paris) 53:1073–1078).

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries, Isolation and Sequencing of cDNA Clones cDNA libraries representing mRNAs from *Buthotus judaicus* telsons were prepared. cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones

ESTs encoding K-channel agonists were identified by conducting BLAST (Basic Local Alignment Search Tool; Altschul et al. (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding K-Channel Modifiers

The BLASTX search using the EST sequence from clone ibj1c.pk007.k8 revealed similarity of the protein encoded by the cDNA to cobatoxin 1 from *Centruroides noxius* (NCBI General Identifier No. 2959750; pLog=5.22). The sequence of a substantial portion of the cDNA insert from clone ibj1c.pk007.k8 is shown in SEQ ID NO:1; the deduced amino acid sequence of this cDNA is shown in SEQ ID NO:2. This amino acid sequence contains a signal sequence (amino acids 1–21) and a mature protein (amino acids 22–58). The amino acid sequence set forth in SEQ ID NO:2 was evaluated by BLASTP, yielding a pLog value of 5.22 versus the *Centruroides noxius* sequence. FIG. 1 presents an alignment of the amino acid sequences set forth in SEQ ID NO:2 and the *Centruroides noxius* sequence (SEQ ID NO:21). The amino acid sequence presented in SEQ ID NO:2 is 36.2% similar to the *Centruroides noxius* sequence.

The BLASTX search using the EST sequence from clones ibj1c.pk006.i20 and ibj1c.pk009.i6 revealed similarity of the protein encoded by the cDNA to kaliotoxin 2 precursor from *Androctonus australis* (NCBI General Identifier No. 1173377; pLog 4.05 and 5.30, respectively). The sequence of a substantial portion of the cDNA insert from clone ibj1c.pk006.i20 is shown in SEQ ID NO:3; the deduced amino acid sequence of this cDNA is shown in SEQ ID NO:4. This amino acid sequence contains a signal sequence (amino acids 1–22) and a mature protein (amino acids 23–61). The amino acid sequence set forth in SEQ ID NO:4 was evaluated by BLASTP, yielding a pLog value of 4.10 versus the *Androctonus australis* sequence. The sequence of a substantial portion of the cDNA insert from clone ibj1c.pk009.i6 is shown in SEQ ID NO:5; the deduced amino acid sequence of this cDNA is shown in SEQ ID NO:6. This amino acid sequence contains a signal sequence (amino acids 1–22) and a mature protein (amino acids 23–59). The amino acid sequence set forth in SEQ ID NO:6 was evaluated by BLASTP, yielding a pLog value of 5.40 versus the *Androctonus australis* sequence. FIG. 2 presents an alignment of the amino acid sequences set forth in SEQ ID NO:4 and SEQ ID NO:6 and the *Androctonus australis* sequence (SEQ ID NO:22). The amino acid sequence presented in SEQ ID NO:4 is 27.1% similar to the *Androctonus australis* sequence and the amino acid sequence presented in SEQ ID NO:6 is 35.6% similar to the *Androctonus australis* sequence.

The BLASTX search using the EST sequence from clone ibj1c.pk008.d3 revealed similarity of the protein encoded by the cDNA to leiuropeptide I from *Leiurus quinquestriatus hebraeus* (NCBI General Identifier No. 1711347; pLog=8.15). The sequence of a substantial portion of the cDNA insert from clone ibj1c.pk008.d3 is shown in SEQ ID NO:7; the deduced amino acid sequence of this cDNA is shown in SEQ ID NO:8. This amino acid sequence contains a signal sequence (amino acids 1–28) and a mature protein (amino acids 29–56). The amino acid sequence set forth in SEQ ID NO:8 was evaluated by BLASTP, yielding a pLog value of 8.15 versus the *Leiurus quinquestriatus hebraeus* sequence. FIG. 3 presents an alignment of the amino acid sequences set forth in SEQ ID NO:8 and the *Leiurus quinquestriatus hebraeus* sequence (SEQ ID NO:23). The amino acid sequence presented in SEQ ID NO:8 is 78.6% similar to the *Leiurus quinquestriatus hebraeus* sequence.

The BLASTX search using the EST sequence from clone ibj1c.pk005.e21 revealed similarity of the protein encoded by the cDNA to leiuropeptide III from *Leiurus quinquestriatus hebraeus* (NCBI General Identifier No. 1711349; pLog=9.70). The sequence of a substantial portion of the cDNA insert from clone ibj1c.pk005.e21 is shown in SEQ ID NO:9; the deduced amino acid sequence of this cDNA is shown in SEQ ID NO:10. This amino acid sequence contains a signal sequence (amino acids 1–30) and a mature protein (amino acids 31–59). The amino acid sequence set forth in SEQ ID NO:10 was evaluated by BLASTP, yielding a pLog value of 10.0 versus the *Leiurus quinquestriatus hebraeus* sequence. FIG. 4 presents an alignment of the amino acid sequences set forth in SEQ ID NO:10 and the *Leiurus quinquestriatus hebraeus* sequence (SEQ ID NO:24). The amino acid sequence presented in SEQ ID NO:10 is 82.8% similar to the *Leiurus quinquestriatus hebraeus* sequence.

The BLASTX search using the EST sequence from clone ibj1c.pk007.c 13 revealed similarity of the protein encoded by the cDNA to leiurotoxin I from *Leiurus quinquestriatus hebraeus* (NCBI General Identifier No. 134302; pLog=9.22). The sequence of a substantial portion of the cDNA insert from clone ibj1c.pk007.c 13 is shown in SEQ ID NO:11; the deduced amino acid sequence of this cDNA is shown in SEQ ID NO:12. This amino acid sequence contains a signal sequence (amino acids 1–37) and a mature protein (amino acids 38–70). The amino acid sequence set forth in SEQ ID NO:12 was evaluated by BLASTP, yielding a pLog value of 9.10 versus the *Leiurus quinquestriatus hebraeus* sequence. FIG. 5 presents an alignment of the amino acid sequences set forth in SEQ ID NO:12 and the *Leiurus quinquestriatus hebraeus* sequence (SEQ ID NO:25). The amino acid sequence presented in SEQ ID NO:12 is 80.6% similar to the *Leiurus quinquestriatus hebraeus* sequence.

The BLASTX search using the EST sequence from clone ibj1c.pk0002.f9 revealed similarity of the protein encoded by the cDNA to neurotoxin P2 from *Androctonus mauretanicus* (NCBI General Identifier No. 134379; pLog=5.10). The sequence of a substantial portion of the cDNA insert from clone ibj1c.pk0002.f9 is shown in SEQ ID NO:13; the deduced amino acid sequence of this cDNA is shown in SEQ ID NO:14. This amino acid sequence contains a signal sequence (amino acids 1–23) and a mature protein (amino acids 24–60). The amino acid sequence set forth in SEQ ID NO:14 was evaluated by BLASTP, yielding a pLog value of 5.15 versus the *Androctonus mauretanicus* sequence. FIG. 6 presents an alignment of the amino acid sequences set forth in SEQ ID NO:14 and the *Androctonus mauretanicus* sequence (SEQ ID NO:26). The amino acid sequence presented in SEQ ID NO:14 is 45.7% similar to the *Androctonus mauretanicus* sequence.

The BLASTX search using the EST sequence from clones ibj1c.pk006.h8 and ibj1c.pk005.n9 revealed similarity of the protein encoded by the cDNA to potassium channel blocking toxin 15-1 from *Leiurus quinquestriatus hebraeus* (NCBI General Identifier No. 1173380; pLog=12). The sequence of a substantial portion of the cDNA insert from clone ibj1c.pk006.h8 is shown in SEQ ID NO:15; the deduced amino acid sequence of this cDNA is shown in SEQ ID NO:16. This amino acid sequence contains a signal sequence (amino acids 1–22) and a mature protein (amino acids 23–58). The amino acid sequence set forth in SEQ ID NO:16 was evaluated by BLASTP, yielding a pLog value of 12.0 versus the *Leiurus quinquestriatus hebraeus* sequence. The sequence of a substantial portion of the cDNA insert from clone ibj1c.pk005.n9 is shown in SEQ ID NO:17; the deduced amino acid sequence of this cDNA is shown in SEQ ID NO:18. This amino acid sequence contains a signal sequence (amino acids 1–22) and a mature protein (amino acids 23–58). The amino acid sequence set forth in SEQ ID NO:18 was evaluated by BLASTP, yielding a pLog value of 12.0 versus the *Leiurus quinquestriatus hebraeus* sequence. FIG. 7 presents an alignment of the amino acid sequences set forth in SEQ ID NO:16 and SEQ ID NO:18 and the *Leiurus quinquestriatus hebraeus* sequence (SEQ ID NO:27). The amino acid sequence presented in SEQ ID NO:16 is 80.6% similar to the *Leiurus quinquestriatus hebraeus* sequence and the amino acid sequence presented in SEQ ID NO:18 is 77.8% similar to the *Leiurus quinquestriatus hebraeus* sequence.

The BLASTX search using the EST sequence from clone ibj1c.pk007.g5 revealed similarity of the protein encoded by the cDNA to Bmtx 1 toxin from *Buthus Martensii* (NCBI General Identifier No. 4389290; pLog=10.15). The sequence of a substantial portion of the cDNA insert from clone ibj1c.pk007.g5 is shown in SEQ ID NO:19; the deduced amino acid sequence of this cDNA is shown in SEQ ID NO:20. This amino acid sequence contains a signal sequence (amino acids 1–20) and a mature protein (amino acids 21–57). The amino acid sequence set forth in SEQ ID NO:20 was evaluated by BLASTP, yielding a pLog value of 10.15 versus the *Buthus Martensii* sequence. FIG. 8 presents an alignment of the amino acid sequences set forth in SEQ ID NO:20 and the *Buthus Martensii* sequence (SEQ ID NO:28). The amino acid sequence presented in SEQ ID NO:20 is 62.2% similar to the *Buthus Martensii* sequence.

The data in Table 2 represents a calculation of the percent similarity of the amino acid sequences set forth in SEQ ID NOs:2, 4, 6, 8, 10, 12, 14, 16, 18 and 20 and the sequences in the NCBI database (SEQ ID NOs:21, 22, 23, 24, 25, 26, 27 and 28).

TABLE 2

Percent Identity of Amino Acid Sequences Deduced From the Nucleotide Sequences of cDNA Clones Encoding Polypeptides Homologous to K-Channel Modifiers

| Clone | SEQ ID NO. | NCBI General Identifier No. | Percent Identity |
|---|---|---|---|
| ibj1c.pk007.k8 | 2 | 2959750 | 36.2 |
| ibj1c.pk006.i20 | 4 | 1173377 | 27.1 |
| ibj1c.pk009.i6 | 6 | 1173377 | 35.6 |
| ibj1c.pk008.d3 | 8 | 1711347 | 78.6 |
| ibj1c.pk005.e21 | 10 | 1711349 | 82.8 |
| ibj1c.pk007.c13 | 12 | 134302 | 80.6 |
| ibj1c.pk0002.f9 | 14 | 134379 | 45.7 |
| ibj1c.pk006.h8 | 16 | 1173380 | 80.6 |
| ibj1c.pk005.n9 | 18 | 1173380 | 77.8 |
| ibj1c.pk007.g5 | 20 | 4389290 | 62.2 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments, BLAST scores and probabilities indicate that the instant nucleic acid fragments encode ten distinct, full-length, scorpion potassium channel modifiers with entire or nearly entire signal sequences: two potassium channel blocking toxin 15-1, a Bmtx toxin, a neurotoxin P2, a leiurotoxin I, a leiuropeptide I, a leiuropeptide III, two kaliotoxin 2 precursors and a cobatoxin 1.

Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (Nco I or Sma I) can be incorporated into the oligonucleotides to provide proper orientation of the DNA fragment when inserted into the digested vector pML103 as described below. Amplification is then performed in a standard PCR. The amplified DNA is then digested with restriction enzymes Nco I and Sma I and fractionated on an agarose gel. The appropriate band can be isolated from the gel and combined with a 4.9 kb Nco I-Sma I fragment of the plasmid pML103. Plasmid pML103 has been deposited under the terms of the Budapest Treaty at ATCC (American Type Culture Collection, 10801 University Blvd., Manassas, Va. 20110–2209), and bears accession number ATCC 97366. The DNA segment from pML 103 contains a 1.05 kb Sal I-Nco I promoter fragment of the maize 27 kD zein gene and a 0.96 kb Sma I-Sal I fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenasem DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al., (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from cauliflower mosaic virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 µm in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a KaptonTM flying disc (Bio-Rad Labs). The particles are then accelerated into the corn tissue with a BiolisticM PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of mercury (Hg). The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al., (1990) *Bio/Technology* 8:833–839).

Example 5

Expression of Chimeric Genes in Dicot Cells

A seed-specific construct composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin construct includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma 1, Kpn I and Xba I. The entire construct is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed construct.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL of liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature (London)* 327:70, U.S. Pat. No. 4,945,050). A Du Pont B PDS1000/HE instrument (helium retrofit) can be used for these transformations.

A selectable marker gene which can be used to facilitate soybean transformation is a chimeric gene composed of the 35S promoter from cauliflower mosaic virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed construct comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µL spermidine (0.1 M), and 50 µL $CaCl_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches of mercury (Hg). The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC, Philadelphia, Pa.). Buffer and agarose contain 10 μg/mL ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/μL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21 (DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25° C. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 7

Expression of Chimeric Genes in Insect Cells

The cDNAs encoding the instant polypeptides may be introduced into the baculovirus genome itself. For this purpose the cDNAs may be placed under the control of the polyhedron promoter, the IE1 promoter, or any other one of the baculovirus promoters. The cDNA, together with appropriate leader sequences is then inserted into a baculovirus transfer vector using standard molecular cloning techniques. Following transformation of E. coli DH5α, isolated colonies are chosen and plasmid DNA is prepared and is analyzed by restriction enzyme analysis. Colonies containing the appropriate fragment are isolated, propagated, and plasmid DNA is prepared for cotransfection.

Spodoptera frugiperda cells (Sf-9) are propagated in ExCell® 401 media (JRH Biosciences, Lenexa, Kans.) supplemented with 3.0% fetal bovine serum. Lipofectin® (50 μL at 0.1 mg/mL, Gibco/BRL) is added to a 50 μL aliquot of the transfer vector containing the toxin gene (500 ng) and linearized polyhedrin-negative AcNPV (2.5 μg, Baculogold® viral DNA, Pharmigen, San Diego, Calif.). Sf-9 cells (approximate 50% monolayer) are co-transfected with the viral DNA/transfer vector solution. The supernatant fluid from the co-transfection experiment is collected at 5 days post-transfection and recombinant viruses are isolated employing standard plaque purification protocols, wherein only polyhedrin-positive plaques are selected (O'Reilly et al. (1992), Baculovirus Expression Vectors: A Laboratory Manual, W. H. Freeman and Company, New York.). Sf-9 cells in 35 mM petri dishes (50% monolayer) are inoculated with 100 μL of a serial dilution of the viral suspension, and supernatant fluids are collected at 5 days post infection. In order to prepare larger quantities of virus for characterization, these supernatant fluids are used to inoculate larger tissue cultures for large scale propagation of recombinant viruses. Expression of the instant polypeptides encoded by the recombinant baculovirus is confirmed by bioassay.

Example 8

Activity of Encoded Peptides Against *Heliothis Virescens*

It has been shown that single amino acids residues are important for receptor binding and for biological activity of K-channel toxins (Sabatier et al. (1994) *Int. J. Peptide Protein Res.* 43:486–495). The cDNAs described herein were cloned into baculoviruses and used to test their activity against Lepidopteran. All ten clones were tested in two independent bioassays and displayed at least some activity against *Heliothis virescens*.

The DNA encoding the peptides was amplified by performing PCR and adding a Bgl II restriction site at the 5' end and an Eco RI site at the 3' end to allow cloning into the baculovirus transfer vector pAcUW21 (BD Biosciences-PharMingen, San Diego, Calif.). After amplification in *E. coli* the presence of the appropriate fragments was confirmed by restriction enzyme analysis. Colonies containing the appropriate fragments were isolated, propagated, and plasmid DNA was prepared for lipofectin-mediated co-transfection into insect cells with linearized polyhedrin-negative AcNPV. Co-transfections were performed essentially as described in Example 7. Polyhedrin-positive recombinant viruses were isolated employing standard plaque purification protocols and were mixed with a plug of HV diet (www.Bio-Serv.com) and fed to *Heliothis virescens* larvae.

Depicted in Table 3 are the results from two independent experiments in which four 5-day-old larvae were fed 200 mg of viral-contaminated diet. The larvae were allowed to eat for 2 days or until the viral-contaminated diet was consumed, then fresh 1 g diet plugs were added to allow continued feeding. Larvae were examined for symptoms at 4, 5, 6, and 7 days after the fresh diet was added and scored as active if the larvae became irritated and had contractions and died, moderately active if the larvae had contractions and a reduction in weight, and slightly active if the larvae had low diet consumption and a retardation in growth. These assays were compared to the results obtained by feeding insects with a diet containing wild-type AcNPV where the larvae die from melt-down after 7 days and by feeding insects with a control diet (water added instead of virus) where all the larvae survive.

TABLE 3

Activity of Scorpion Potassium Channel Modifiers on *Heliothis virescens* Larvae

| Clone | Experiment 1 | Experiment 2 |
| --- | --- | --- |
| ibj1c.pk007.k8 | Slightly Active | Slightly Active |
| ibj1c.pk006.i20 | Slightly Active | Slightly Active |
| ibj1c.pk009.i6 | Slightly Active | Slightly Active |
| ibj1c.pk008.d3 | Slightly Active | Slightly Active |
| ibj1c.pk005.e21 | Slightly Active | Active |
| ibj1c.pk007.c13 | Slightly Active | Slightly Active |
| ibj1c.pk0002.f9 | Slightly Active | Slightly Active |
| ibj1c.pk006.h8 | Slightly Active | Active |
| ibj1c.pk005.n9 | Slightly Active | Slightly Active |
| ibj1c.pk007.g5 | Slightly Active | Moderately Active |

In summary, the peptides encoded by the scorpion sequences depicted in SEQ ID NOs:2, 4, 6, 8, 10, 12, 14, 16, 18, and 20 showed toxic activity against the lepidopteran *Heliothis virescens*.

What is claimed is:

1. An isolated polynucleotide comprising:
   (a) a nucleotide sequence encoding a polypeptide having toxin activity, wherein the amino acid sequence of the polypeptide has the amino acid sequence of SEQ ID NO:2, or
   (b) the complement of the nucleotide sequence, wherein the complement and the nucleotide sequence contain the same number of nucleotides and are 100% complementary.

2. The polynucleotide of claim 1 wherein the nucleotide sequence comprises the nucleotide sequence of SEQ ID NO:1.

3. A method for isolating a polypeptide encoded by the polynucleotide of claim 1 comprising isolating the polypeptide from a cell containing a recombinant DNA construct comprising the polynucleotide operably linked to a regulatory sequence.

4. An isolated polynucleotide comprising:
   (a) a nucleotide sequence encoding a polypeptide having toxin activity, wherein the amino acid sequence of the polypeptide comprises amino acids 22–58 of the amino acid sequence of SEQ ID NO:2, or
   (b) the complement of the nucleotide sequence, wherein the complement and the nucleotide sequence contain the same number of nucleotides and are 100% complementary.

5. A vector comprising the polynucleotide of claim 1 or claim 4.

6. A recombinant DNA construct comprising the polynucleotide of claim 1 or claim 4 operably linked to a regulatory sequence.

7. A cell comprising the recombinant DNA construct of claim 6.

8. A method for transforming a cell comprising transforming a cell with the polynucleotide of claim 1 or claim 4.

* * * * *

SEQUENCE LISTING

<160> NUMBER OF SEQ ID NOS: 28

<210> SEQ ID NO 1
<211> LENGTH: 177
<212> TYPE: DNA
<213> ORGANISM: Hottentotta judaica

<400> SEQUENCE: 1

```
atgagccgta ttttcacaat catcttaatt gtattcgcct taaatataat tatttcttta      60
tctaatttta aagtggaagc agctcaatgc tattccagtg attgtagagt gaaatgtgcc     120
gctatgggat tcaactcagg aaaatgtata aacagtaaat gtaaatgcta taaataa       177
```

<210> SEQ ID NO 2
<211> LENGTH: 58
<212> TYPE: PRT
<213> ORGANISM: Hottentotta judaica

<400> SEQUENCE: 2

```
Met Ser Arg Ile Phe Thr Ile Ile Leu Ile Val Phe Ala Leu Asn Ile
  1               5                  10                  15

Ile Ile Ser Leu Ser Asn Phe Lys Val Glu Ala Ala Gln Cys Tyr Ser
             20                  25                  30

Ser Asp Cys Arg Val Lys Cys Ala Ala Met Gly Phe Asn Ser Gly Lys
         35                  40                  45

Cys Ile Asn Ser Lys Cys Lys Cys Tyr Lys
     50                  55
```

<210> SEQ ID NO 3

<210> SEQ ID NO 3
<211> LENGTH: 186
<212> TYPE: DNA
<213> ORGANISM: Hottentotta judaica

<400> SEQUENCE: 3

```
atgaaatttt ttacttcagt tctaatgatg atgataattt tctcaatggt tatttcgagc      60
cacgctcaat acgagttgga tgtaacgtgt atgggaggag cagataattg cgtaaaacca     120
tgctatgata aatacggcac aactaaaact aaatgcatca acgatcggtg caactgttat     180
ccgtaa                                                                186
```

<210> SEQ ID NO 4
<211> LENGTH: 61
<212> TYPE: PRT
<213> ORGANISM: Hottentotta judaica

<400> SEQUENCE: 4

```
Met Lys Phe Phe Thr Ser Val Leu Met Met Met Ile Ile Phe Ser Met
  1               5                  10                  15

Val Ile Ser Ser His Ala Gln Tyr Glu Leu Asp Val Thr Cys Met Gly
                 20                  25                  30

Gly Ala Asp Asn Cys Val Lys Pro Cys Tyr Asp Lys Tyr Gly Thr Thr
             35                  40                  45

Lys Thr Lys Cys Ile Asn Asp Arg Cys Asn Cys Tyr Pro
         50                  55                  60
```

<210> SEQ ID NO 5
<211> LENGTH: 180
<212> TYPE: DNA
<213> ORGANISM: Hottentotta judaica

<400> SEQUENCE: 5

```
atgaagtttt cttcaattat tctattaact ctccttatct gttcaatgac catatgtatt      60
aattgccaag tagaaacaaa tgtgaaatgt acaggtggct catgtgcttc aacatgtaaa     120
agagtaatag gagtagctgc aggaaaatgc attaatggaa gatgtgtctg ctatccgtag     180
```

<210> SEQ ID NO 6
<211> LENGTH: 59
<212> TYPE: PRT
<213> ORGANISM: Hottentotta judaica

<400> SEQUENCE: 6

```
Met Lys Phe Ser Ser Ile Ile Leu Leu Thr Leu Leu Ile Cys Ser Met
  1               5                  10                  15

Thr Ile Cys Ile Asn Cys Gln Val Glu Thr Asn Val Lys Cys Thr Gly
                 20                  25                  30

Gly Ser Cys Ala Ser Thr Cys Lys Arg Val Ile Gly Val Ala Ala Gly
             35                  40                  45

Lys Cys Ile Asn Gly Arg Cys Val Cys Tyr Pro
         50                  55
```

<210> SEQ ID NO 7
<211> LENGTH: 171
<212> TYPE: DNA
<213> ORGANISM: Hottentotta judaica

<400> SEQUENCE: 7

```
atgagtcgtt tgtttacact ggttttaatt gtattggcca tgaacgtgat gatggctatt      60
atatcggatc ctggagtgga agctgttgat tgtgaagaat gccctttca ttgcgcaggc     120
```

```
aaaaacgcca tacctacctg cgatgatggc gagtgtaact gcaacgtatg a         171
```

<210> SEQ ID NO 8
<211> LENGTH: 56
<212> TYPE: PRT
<213> ORGANISM: Hottentotta judaica

<400> SEQUENCE: 8

```
Met Ser Arg Leu Phe Thr Leu Val Leu Ile Val Leu Ala Met Asn Val
 1               5                  10                  15

Met Met Ala Ile Ile Ser Asp Pro Gly Val Glu Ala Val Asp Cys Glu
             20                  25                  30

Glu Cys Pro Phe His Cys Ala Gly Lys Asn Ala Ile Pro Thr Cys Asp
         35                  40                  45

Asp Gly Glu Cys Asn Cys Asn Val
     50                  55
```

<210> SEQ ID NO 9
<211> LENGTH: 180
<212> TYPE: DNA
<213> ORGANISM: Hottentotta judaica

<400> SEQUENCE: 9

```
atgaaaatga gccgtcttta tgcaatcatc ttaattgttc ttgtcatgaa tgtaattatg      60
acaattatgc ctgattcgaa agtagaagct gttggttgtg aagattgccc tgagcactgt    120
tcccagcaaa atgcccgagc aaaatgtgaa atgacaaat gtgtatgcga acctaaatga     180
```

<210> SEQ ID NO 10
<211> LENGTH: 59
<212> TYPE: PRT
<213> ORGANISM: Hottentotta judaica

<400> SEQUENCE: 10

```
Met Lys Met Ser Arg Leu Tyr Ala Ile Ile Leu Ile Val Leu Val Met
 1               5                  10                  15

Asn Val Ile Met Thr Ile Met Pro Asp Ser Lys Val Glu Ala Val Gly
             20                  25                  30

Cys Glu Asp Cys Pro Glu His Cys Ser Gln Gln Asn Ala Arg Ala Lys
         35                  40                  45

Cys Glu Asn Asp Lys Cys Val Cys Glu Pro Lys
     50                  55
```

<210> SEQ ID NO 11
<211> LENGTH: 213
<212> TYPE: DNA
<213> ORGANISM: Hottentotta judaica

<400> SEQUENCE: 11

```
atgataaagg aattattatc tacagaaatg tacaattact acaaatttgt tttaattatg      60
gttgtgttct ttgcagctac aattattttc tctgatataa atgtagaagg tgcattttgt    120
aatcttagaa ggtgtcagtt aatttgtaga gaaagtggat tattaggaaa gtgcattgga    180
gatagatgcg aatgtgttcc acatggcaaa taa                                 213
```

<210> SEQ ID NO 12
<211> LENGTH: 70
<212> TYPE: PRT
<213> ORGANISM: Hottentotta judaica -continued

<400> SEQUENCE: 12

Met Ile Lys Glu Leu Leu Ser Thr Glu Met Tyr Asn Tyr Tyr Lys Phe
1               5                   10                  15

Val Leu Ile Met Val Phe Phe Ala Ala Thr Ile Ile Phe Ser Asp
            20                  25                  30

Ile Asn Val Glu Gly Ala Phe Cys Asn Leu Arg Arg Cys Gln Leu Ile
        35                  40                  45

Cys Arg Glu Ser Gly Leu Leu Gly Lys Cys Ile Gly Asp Arg Cys Glu
50                  55                  60

Cys Val Pro His Gly Lys
65                  70

<210> SEQ ID NO 13
<211> LENGTH: 186
<212> TYPE: DNA
<213> ORGANISM: Hottentotta judaica

<400> SEQUENCE: 13
atgaagtttc tctatggaat cattttgatt gctcttttct taactgtaat gattgcaact      60
cattctgaag ctcgttgtcc taattgcttt acaacaaatc cgaatgcaga agctgattgt     120
aagaaatgtt gcggaaatag gtggggaaaa tgtgctggtt atcagtgcgt ctgtccaatg     180
aagtaa                                                                186

<210> SEQ ID NO 14
<211> LENGTH: 61
<212> TYPE: PRT
<213> ORGANISM: Hottentotta judaica

<400> SEQUENCE: 14

Met Lys Phe Leu Tyr Gly Ile Ile Leu Ile Ala Leu Phe Leu Thr Val
1               5                   10                  15

Met Ile Ala Thr His Ser Glu Ala Arg Cys Pro Asn Cys Phe Thr Thr
            20                  25                  30

Asn Pro Asn Ala Glu Ala Asp Cys Lys Lys Cys Cys Gly Asn Arg Trp
        35                  40                  45

Gly Lys Cys Ala Gly Tyr Gln Cys Val Cys Pro Met Lys
    50                  55                  60

<210> SEQ ID NO 15
<211> LENGTH: 176
<212> TYPE: DNA
<213> ORGANISM: Hottentotta judaica

<400> SEQUENCE: 15
atgaaaattt tgtctgttct tttgatagct ctgattattt gctcattggg cgtttgtata      60
gaagctggac ttatagacgt aagatgtagt gcctctcgtg aatgttggga agcttgcaga     120
aaagtaacag gatcaggaca aggaaagtgc cagaataacc aatgtcgttg ttatta         176

<210> SEQ ID NO 16
<211> LENGTH: 58
<212> TYPE: PRT
<213> ORGANISM: Hottentotta judaica

<400> SEQUENCE: 16

Met Lys Ile Leu Ser Val Leu Leu Ile Ala Leu Ile Ile Cys Ser Leu
1               5                   10                  15

Gly Val Cys Ile Glu Ala Gly Leu Ile Asp Val Arg Cys Ser Ala Ser

```
                    20                  25                  30
Arg Glu Cys Trp Glu Ala Cys Arg Lys Val Thr Gly Ser Gly Gln Gly
             35                  40                  45

Lys Cys Gln Asn Asn Gln Cys Arg Cys Tyr
         50                  55
```

<210> SEQ ID NO 17
<211> LENGTH: 177
<212> TYPE: DNA
<213> ORGANISM: Hottentotta judaica

<400> SEQUENCE: 17

```
atgaaaattt tatctgttct tttgatagct ctcataatct gttcaataag tatttatagt    60
gaagctgatc ttatagacgt aaaatgtatt tcatctcaag aatgttggat tgcttgtaaa   120
aaagtaactg gacggtttca aggaaaatgc cagaataaac aatgtcgctg ttattaa     177
```

<210> SEQ ID NO 18
<211> LENGTH: 58
<212> TYPE: PRT
<213> ORGANISM: Hottentotta judaica

<400> SEQUENCE: 18

```
Met Lys Ile Leu Ser Val Leu Leu Ile Ala Leu Ile Ile Cys Ser Ile
 1               5                  10                  15

Ser Ile Tyr Ser Glu Ala Asp Leu Ile Asp Val Lys Cys Ile Ser Ser
             20                  25                  30

Gln Glu Cys Trp Ile Ala Cys Lys Lys Val Thr Gly Arg Phe Gln Gly
         35                  40                  45

Lys Cys Gln Asn Lys Gln Cys Arg Cys Tyr
     50                  55
```

<210> SEQ ID NO 19
<211> LENGTH: 174
<212> TYPE: DNA
<213> ORGANISM: Hottentotta judaica
<220> FEATURE:
<221> NAME/KEY: unsure
<222> LOCATION: (9)
<220> FEATURE:
<221> NAME/KEY: unsure
<222> LOCATION: (88)

<400> SEQUENCE: 19

```
attttatcng tttttctgat tactttcgta atctgttcga taatgatttc aaccgaagct    60
cagtttatag acgtgaaatg cacatcanct aaggaatgtt ggcctatttg taaggaaaga   120
tttggtgtgg ccagaggaaa gtgcataaat aagcaatgcc gttgttattc gtaa        174
```

<210> SEQ ID NO 20
<211> LENGTH: 57
<212> TYPE: PRT
<213> ORGANISM: Hottentotta judaica
<220> FEATURE:
<221> NAME/KEY: UNSURE
<222> LOCATION: (30)

<400> SEQUENCE: 20

```
Ile Leu Ser Val Phe Leu Ile Thr Phe Val Ile Cys Ser Ile Met Ile
 1               5                  10                  15

Ser Thr Glu Ala Gln Phe Ile Asp Val Lys Cys Thr Ser Xaa Lys Glu
             20                  25                  30
```

```
Cys Trp Pro Ile Cys Lys Glu Arg Phe Gly Val Ala Arg Gly Lys Cys
         35                  40                  45

Ile Asn Lys Gln Cys Arg Cys Tyr Ser
         50                  55

<210> SEQ ID NO 21
<211> LENGTH: 62
<212> TYPE: PRT
<213> ORGANISM: Centruroides noxius

<400> SEQUENCE: 21

Met Glu Gly Ile Ala Lys Ile Thr Leu Ile Leu Phe Leu Phe Val
  1               5                  10                  15

Thr Met His Thr Phe Ala Asn Trp Asn Thr Glu Ala Ala Val Cys Val
                 20                  25                  30

Tyr Arg Thr Cys Asp Lys Asp Cys Lys Arg Arg Gly Tyr Arg Ser Gly
         35                  40                  45

Lys Cys Ile Asn Asn Ala Cys Lys Cys Tyr Pro Tyr Gly Lys
         50                  55                  60

<210> SEQ ID NO 22
<211> LENGTH: 59
<212> TYPE: PRT
<213> ORGANISM: Androctonus australis

<400> SEQUENCE: 22

Met Lys Val Phe Ser Ala Val Leu Ile Ile Leu Phe Val Cys Ser Met
  1               5                  10                  15

Ile Ile Gly Ile Asn Ala Val Arg Ile Pro Val Ser Cys Lys His Ser
                 20                  25                  30

Gly Gln Cys Leu Lys Pro Cys Lys Asp Ala Gly Met Arg Phe Gly Lys
         35                  40                  45

Cys Met Asn Gly Lys Cys Asp Cys Thr Pro Lys
         50                  55

<210> SEQ ID NO 23
<211> LENGTH: 28
<212> TYPE: PRT
<213> ORGANISM: Leiurus quinquestriatus

<400> SEQUENCE: 23

Val Gly Cys Glu Glu Cys Pro Met His Cys Lys Gly Lys Asn Ala Lys
  1               5                  10                  15

Pro Thr Cys Asp Asn Gly Val Cys Asn Cys Asn Val
                 20                  25

<210> SEQ ID NO 24
<211> LENGTH: 29
<212> TYPE: PRT
<213> ORGANISM: Leiurus quinquestriatus

<400> SEQUENCE: 24

Val Ser Cys Glu Asp Cys Pro Asp His Cys Ser Thr Gln Lys Ala Arg
  1               5                  10                  15

Ala Lys Cys Asp Asn Asp Lys Cys Val Cys Glu Pro Lys
                 20                  25

<210> SEQ ID NO 25
<211> LENGTH: 31
<212> TYPE: PRT
<213> ORGANISM: Leiurus quinquestriatus
```

-continued

```
<400> SEQUENCE: 25

Ala Phe Cys Asn Leu Arg Met Cys Gln Leu Ser Cys Arg Ser Leu Gly
 1               5                  10                  15

Leu Leu Gly Lys Cys Ile Gly Asp Lys Cys Glu Cys Val Lys His
             20                  25                  30

<210> SEQ ID NO 26
<211> LENGTH: 35
<212> TYPE: PRT
<213> ORGANISM: Androctonus mauretanicus

<400> SEQUENCE: 26

Cys Gly Pro Cys Phe Thr Thr Asp Pro Tyr Thr Glu Ser Lys Cys Ala
 1               5                  10                  15

Thr Cys Cys Gly Gly Arg Gly Lys Cys Val Gly Pro Gln Cys Leu Cys
             20                  25                  30

Asn Arg Ile
         35

<210> SEQ ID NO 27
<211> LENGTH: 36
<212> TYPE: PRT
<213> ORGANISM: Leiurus quinquestriatus

<400> SEQUENCE: 27

Gly Leu Ile Asp Val Arg Cys Tyr Asp Ser Arg Gln Cys Trp Ile Ala
 1               5                  10                  15

Cys Lys Lys Val Thr Gly Ser Thr Gln Gly Lys Cys Gln Asn Lys Gln
             20                  25                  30

Cys Arg Cys Tyr
         35

<210> SEQ ID NO 28
<211> LENGTH: 37
<212> TYPE: PRT
<213> ORGANISM: Buthus martensii

<400> SEQUENCE: 28

Xaa Phe Thr Asp Val Lys Cys Thr Gly Ser Lys Gln Cys Trp Pro Val
 1               5                  10                  15

Cys Lys Gln Met Phe Gly Lys Pro Asn Gly Lys Cys Met Asn Gly Lys
             20                  25                  30

Cys Arg Cys Tyr Ser
         35
```